US007941000B2

United States Patent
Rongen et al.

(10) Patent No.: US 7,941,000 B2
(45) Date of Patent: May 10, 2011

(54) METHOD FOR PRODUCING AN IMAGE AND SYSTEM FOR PRODUCING AN IMAGE

(75) Inventors: Peter Maria Johannes Rongen, Eindhoven (NL); Nicolaas Hylke Bakker, Eindhoven (NL); Herman Stegehuis, Best (NL); Peter Willem van den Houten, Eindhoven (NL); Raoul Florent, Ville d'Avray (FR)

(73) Assignee: Koninklijke Philips Electronics N.V., Eindhoven (NL)

(*) Notice: Subject to any disclaimer, the term of this patent is extended or adjusted under 35 U.S.C. 154(b) by 1014 days.

(21) Appl. No.: 11/747,394

(22) Filed: May 11, 2007

(65) Prior Publication Data

US 2008/0279476 A1    Nov. 13, 2008

(51) Int. Cl.
*G06K 9/36* (2006.01)
*G06K 9/00* (2006.01)
*G01N 23/04* (2006.01)
*H05G 1/64* (2006.01)

(52) U.S. Cl. .......... 382/294; 382/128; 382/284; 378/62; 378/98.11; 378/98.12; 128/922

(58) Field of Classification Search .................. None
See application file for complete search history.

(56) References Cited

U.S. PATENT DOCUMENTS

| 6,532,380 | B1 | 3/2003 | Close et al. | |
|---|---|---|---|---|
| 7,415,169 | B2* | 8/2008 | Florent et al. | 382/294 |
| 2008/0008401 | A1* | 1/2008 | Zhu et al. | 382/294 |
| 2008/0063301 | A1* | 3/2008 | Bogoni et al. | 382/294 |
| 2008/0292214 | A1* | 11/2008 | Vomweg et al. | 382/294 |

FOREIGN PATENT DOCUMENTS

WO    WO03045263    6/2003

OTHER PUBLICATIONS

K. Rohr, "Elastic Registration of Multimodial Medical Images: A Survey", Kunstliche Intelligenz, Heft 3/00, arenDTaP Verlag, Bremen, pp. 11-17.
Frangi et al, "Multiscale Vessel Enhancement Filtering", MICCAI 1998, Boston USA, vol. 1496, pp. 130-137, 1998.

* cited by examiner

*Primary Examiner* — Anand Bhatnagar
*Assistant Examiner* — Randolph Chu (57) ABSTRACT

An image of a physical object is produced by receiving a plurality of raw images, dividing the plurality of raw images into a first subset of primary images and a second subset of secondary images according to a predetermined criterion. From the first subset of primary images an intermediate image is determined while from the second subset of secondary images a mask image is determined. Afterwards a registration of the intermediate image and the mask image is performed by using direct registration of predetermined features present in the intermediate image and the mask image. A fused image of the physical object is generated out of the mask image and the intermediate image.

20 Claims, 6 Drawing Sheets

METHOD FOR PRODUCING AN IMAGE AND SYSTEM FOR PRODUCING AN IMAGE

The invention relates to a method for producing an image, a system for producing an image, a computer readable medium and a program element, in particular to a method for producing an image of a physical object, e.g. a stent.

Methods for producing an image of a physical object are widespread in several technical fields, e.g. the medical field. One example of the medical field is the field of coronary stents. It is of prime importance that a coronary stent is fully expanded and in full contact with the vessel wall after placement in a coronary stenotic lesion. Furthermore, correct positioning of the stent with respect to side branches is crucial. However, a stent is not always clearly visible under fluoroscopy or in an exposure (cine) run. Improvement of stent visibility in X-ray exposure runs might thus facilitate the interventional cardiologist in judging the clinical success of the intervention.

A technique for automatically enhance stent visibility by means of image processing is disclosed in WO 03/045263, for example. A corresponding product is sold and can be used to evaluate proper stent deployment. Although, the visibility of the stent itself may be enhanced the generated image may not provide the cardiologist with enough information.

It may be desirable to provide an alternative method for producing an image, a system for producing an image, a computer readable medium and a program element, which may be further enhanced and may provide more information of the physical object.

This need may be met by a method for producing an image, a system for producing an image, a computer readable medium and a program element, according to the independent claims.

According to an exemplary embodiment a method for producing an image of a physical object comprises receiving a plurality of raw images, dividing the plurality of raw images into a first subset of primary images and a second subset of secondary images according to a predetermined criterion. From the first subset of primary images an intermediate image is determined while from the second subset of secondary images a mask image is determined. Afterwards a registration of the intermediate image and the mask image is performed by using direct registration of predetermined features present in the intermediate image and the mask image and a final image of the physical object is generated by subtracting the mask image and the intermediate image from each other. Preferably, the method further comprise receiving a plurality of raw data sets, each representing one raw image of the physical object, and fusing the mask image and the intermediate image.

According to an exemplary embodiment a system for producing an image of a physical object is provided. The system comprises a generation unit, a processing unit, and a determination unit, wherein the processing unit is adapted to divide a plurality of raw images into a first subset of primary images and a second subset of secondary images according to a predetermined criterion. Further, the determining unit is adapted to determine an intermediate image from the first subset of primary images and is further adapted to determine a mask image from the second subset of secondary images. The processing unit is adapted to register the intermediate image and the mask image by using direct registration of predetermined features present in the intermediate image and the mask image. Furthermore, the generation unit is adapted to fuse the mask image and the intermediate image. Preferably, the generation unit is further adapted to generate the plurality of raw images from a plurality of raw data sets.

According to an exemplary embodiment a computer readable medium, in which a program for producing an image based on raw images is stored, is provided, which program, when executed by a processor, is adapted to control a method comprising receiving a plurality of raw images, dividing the plurality of raw images into a first subset of primary images and a second subset of secondary images according to a predetermined criterion. From the first subset of primary images an intermediate image is determined while from the second subset of secondary images a mask image is determined. Afterwards a registration of the intermediate image and the mask image is performed by using direct registration of predetermined features present in the intermediate image and the mask image and a fusing of the mask image and the intermediate image is performed. Preferably, the method further comprise receiving a plurality of raw data sets, each representing one raw image of the physical object, and generating the plurality of raw images from the raw data sets.

According to an exemplary embodiment a program element for producing an image, based on raw images, is provided, which program, when executed by a processor, is adapted to control a method comprising receiving a plurality of raw images, dividing the plurality of raw images into a first subset of primary images and a second subset of secondary images according to a predetermined criterion. From the first subset of primary images an intermediate image is determined while from the second subset of secondary images a mask image is determined. Afterwards a registration of the intermediate image and the mask image is performed by using direct registration of predetermined features present in the intermediate image and the mask image and a fusing of the mask image and the intermediate image is performed. Preferably, the method further comprise receiving a plurality of raw data sets, each representing one raw image of the physical object, and generating the plurality of raw images from the raw data sets.

It may be seen as the gist of an exemplary embodiment of the present invention that a method for generating an image of a physical object, for example a stent introduced in a coronary vessel, is provided, wherein two different images are superimposed, e.g. subtracted from each other, in order to generate an image which shows more clearly features of the physical object. For example, one image may depict a stent more clearly, while the other image depict the coronary vessel more clearly due to specialized recording and/or analysing which is performed with the corresponding data sets. These two images are registered by direct registration, i.e. by mapping defined features in one image to the same features in the other image. Such a direct registration of features in the different images provides a simple and robust method for superimposing different images showing the same physical object, in particular such a direct registration is less complex and processing time consuming than a so called "motion layer decomposition" Motion layer decomposition is used to discriminate between multiple arbitrary layers of motion on the basis of gray scale intensity values, using correlation techniques, while according to this embodiment techniques essentially using a feature that is already known to move along with the object of interest, e.g. the stent and the neighbouring vessel, are used. Afterwards the two images can be fused in order to achieve an image showing both, the stent and the coronary vessel, in an improved quality. That is, a final display of the physical object may be generated by visually fusing the mask image and the intermediate image.

Image registration, which is also called image matching, is well known to the person skilled in the art and refers to the task to compute spatial transformations, which map each point of an image onto its (physically) corresponding point of another image. The three basic operations to realize this image registration are translation, rotation and stretching. Some information about these methods can be gathered from the review article "Elastic Registration of Multimodial Medical Images: A Survey", K. Rohr, Künstliche Intelligenz, Heft 3/00, arenDTaP Verlag, Bremen, pg. 11 to 17 and the references cited therein, which are herein incorporated in whole by reference.

By using the method according to an exemplary embodiment a method may be provided according which an enhanced image of different parts of a physical object may be generateable and/or displayable e, e.g. an enhanced view of a stent, while also including the information of a coronary vessel, in which the stent is introduced. Since both parts may be visible in the final image, it may be possible to evaluate correct placement, e.g. in a longitudinal direction, of the stent in the coronary vessel, and/or to see a correct apposition of the stent to the vessel wall.

In the following, further exemplary embodiments of the method for generating an image of a physical object will be described. However, these embodiments apply also for the system, the computer readable medium and the program element.

According to another exemplary embodiment of the method the fusing is done by one of the group consisting of subtracting the intermediate image and the mask image from each other, overlaying the intermediate image and the mask image, and displaying the intermediate image and the mask image in a spatial and/or temporal interlaced way. The displaying can be done in a blinking mode, a fading mode, a toggling or a moving blinds mode, for example.

By subtracting the two images from each other a final image may be generated showing both, the stent and the coronary vessel, in an improved quality. By displaying the intermediate image and the mask image in a fusing mode, like blinking, fading, toggling or moving blind mode, an efficient and convenient way to display the information of both images on a display.

According to another exemplary embodiment of the method determining the intermediate image comprises averaging a plurality of the primary images.

Such an averaging of a plurality of primary images may provide an image of the physical object, e.g. stent, having improved quality. The averaging may include a registration step as well, i.e. a step in which each point of each image of the plurality of primary images is mapped onto its (physically) corresponding point of another image of the plurality of primary images. The registration may be performed by using said predetermined features in the primary images. Such an averaging may be in particular advantageous since areas in the direct environment of the predetermined features that have a fixed position with respect to the predetermined features may be frozen as well as the predetermined features, while the environment situated further away from the predetermined features may move from one primary image to the next primary image, e.g. due to motion of the heart and/or respiration. Averaging of the frozen primary images, which can be called frames as well, may lead thus to a much enhanced contrast of the environment of the predetermined features, e.g. markers or characteristic structures, like well defined boundaries, and therefore of the stent, whereas all structures and noise of surrounding areas may be smoothed out with a subsequent loss of contrast. In this way the visibility of the stent may be much enhanced. Besides the markers, another feature can also comprise the guide wire, along which the stent balloon with markers is transported to the lesion, for example. Alternatively, other features in the image, that are already known not to belong to the balloon, might be used to exclude image portions from the actual region of boosting and registration.

According to another exemplary embodiment of the method the predetermined criterion is an image intensity in the raw images.

The image intensity may be a suitable criterion to divide the raw data into two different raw images subsets, wherein one raw images subset may represent primary images, while the other raw image subset may represent secondary images. The image intensity may be an average brightness and/or average contrast present in the raw images and/or an intensity in an image derived from the raw image, or even other feature images that represent the presence of contrast agent in the image, in particular regions close to the predetermined features.

According to another exemplary embodiment of the method determining the mask image comprises registering and combining several second images. Such a combining may be implemented by using simple averaging and/or matched filtering.

According to this exemplary embodiment the information of several secondary images may be used to generate a single mask image which may lead to an improved Signal-To-Noise ration in the mask image which may be used afterwards in generating the final image. Thus, a final image exhibiting better quality may be provided.

According to another exemplary embodiment of the method the predetermined features are markers present in the intermediate image and the mask image. Preferably, two markers are used in order to achieve a unique mapping (registration) of the different images. The markers might comprise radiopaque material. In general a marker may be an element which can be arranged on an object and which can be detected in an easy way, e.g. easier as the object itself. By using such a marker it may be possible to perform the registration in an easy and efficient way.

According to another exemplary embodiment of the method the plurality of raw images is generated from a plurality of raw data sets which are recorded in at least two raw data recording runs. In particular, the raw data of the first subset of raw images may be recorded in another run than the raw data of the second subset of raw images. The two runs may be separated by a predetermined time span and/or by a predetermined action, e.g. injection of a contrast agent, in case the physical object comprises a stent and coronary vessels.

According to another exemplary embodiment of the method the raw images belonging to the second subset of second images are recorded under influence of a contrast agent. For example, the raw data belonging to the second subset of second images are recorded under influence of the contrast agent. Preferably, the raw data of the images belonging to the first subset of primary images are recorded under the absence of a contrast agent.

Using such a contrast agent may be an efficient way to provide a mask image on which objects may be seen which may not be seen without the use of the contrast agent, e.g. coronary vessels. By combining, e.g. subtracting, such a mask image from the intermediate image, e.g. an image of a stent, a final image having an improved quality may be provided.

According to another exemplary embodiment the method further comprises determining a plurality of mask images from the second subset of secondary images, and generating a plurality of final images by subtracting the intermediate image and the plurality of mask images from each other. For example, one mask image is determined from each secondary image.

By determining several mask images which can be subtracted from the intermediate image it may be possible to provide a plurality of final images, which may be displayed in a consecutive way afterwards. Thus, in the case of images of a stent and coronary vessels, an automatic flow analysis/visualisation of a contrast agent around the predetermined features, e.g. markers, may be possible, in particular by making explicit use of the positions of the predetermined features and an enhancing technique, e.g. averaging the plurality of primary images.

According to another exemplary embodiment the method further comprises segmenting the intermediate image into at least a first part of the intermediate image and a second part of the intermediate image and segmenting the mask image into at least a first part of the mask image and a second part of the mask image. Further, the final image is generated by subtracting the first part of the intermediate image and the first part of the mask image from each other.

By segmenting the intermediate image and the mask image into at least two parts it may be possible to further increase the quality of the final image, in particular in cutting out areas of interest in both of the images which are then overlaid (subtracted) on each other in order to achieve the final image. For example, in the intermediate image the areas showing a stent may cut out and overlaid on the areas of the mask image showing coronary vessels. That is the areas of the intermediate image which does not relate to the stent are not employed to generate the final image and the areas of the mask image which does not relate to the coronary vessels are not employed to generate the final image.

According to another exemplary embodiment of the method the physical object comprises a first component and a second component, and the method further comprises detecting the first component in the intermediate image, detecting a second border of the second component in the mask image and displaying the relative positions of the first and second component with respect to each other in a graphical or numerical way. Preferably, a first border of the first component and a second border of the second component can be detected. Thus, a border detection can be implemented as an automatic border detection. By comparing only the border of the first component, e.g. a stent, and the border or contour of the second component, e.g. a vessel, it may be easier to recognize mal-apposition of the first component, e.g. stent, with respect to the second component, e.g. vessel. Apart from the borders of the objects it is also possible to detect/segment the complete objects themselves and display them in an overlay mode.

In the following, further exemplary embodiments of the system for producing an image of a physical object will be described. However, these embodiments apply also for the method, the computer readable medium and the program element.

According to another exemplary embodiment the system further comprises a display unit, wherein the system is adapted to display the final image of the physical object on the display unit. For example, the processing unit may be adapted in the above mentioned way.

According to another exemplary embodiment of the system the system is further adapted in such a way that the final image and the intermediate image are displayed on the display unit in an alternating sequence. The alternating sequence may be controlled by the processing unit, i.e. automatically, in such a way that the final image and the intermediate image are interchangeably displayed for a predetermined time span each, i.e. in a so-called "blinking mode".

According to another exemplary embodiment the system further comprises a switch, wherein the switch is adapted in such a way that by the switch it is determinable which image out of the group of images consisting of the intermediate image, the mask image, and the final image is displayed on the display unit. That is, it may be possible to manually switch between the displaying of the final image and the intermediate image, i.e. in a so-called "toggle mode".

The blinking and/or toggle mode may be advantageous in medical use e.g. to improve assessment of a stent placement in relation to a vessel.

According to another exemplary embodiment of the system the system is adapted to generate a plurality of final images out of a plurality of mask images and the intermediate image, and the system is further adapted to display the plurality of final images in a consecutive sequence on the display.

Thus, it might be possible to display a so-called Cine-loop, which may be advantageous to display a motion. For example, in the case of a stent and coronary vessels it may be possible to visualizing an inflow of a contrast agent into the stent.

The generation of the image of a physical object, e.g. the reconstruction of coronary vessels and a stent, by using data taken by a scanning unit and/or an X-ray system, may be realized by a computer program, i.e. by software, or by using one or more special electronic optimization circuits, i.e. in hardware, or in hybrid form, i.e. by software components and hardware components. The computer program may be written in any suitable programming language, such as, for example, C++ and may be stored on a computer-readable medium, such as a CD-ROM. Also, the computer program may be available from a network, such as the Worldwide Web, from which it may be downloaded into image processing units or processors, or any suitable computers.

It may be seen as the gist of an exemplary embodiment of the present invention that a method for producing or generating an image is provided in which two images reconstructed from data taken under different circumstances from the same physical object are registered or matched and afterwards subtracted from each other. This may lead to an enhanced final image. For example, one of the images may be generated by the known StentBoost™ technique which is based on the automatic recognition of two radiopaque markers in all frames of an exposure. The markers can be on a balloon catheter used for stent placement. Immediately after stent expansion, the catheter may be kept in steady position inside the stent, with deflated balloon, and an exposure run may be acquired using the cardio X-ray system of the catheter laboratory. After this the catheter may be removed. Next, the data taken in the run may be transferred to a PC workstation running stent image enhancement software for off-line processing.

The software may freeze the position and orientation of the markers (with respect to each other) at the centre of the monitor screen in every frame (image) of the run and may match the position of the markers to the positions in the first frame. The three basic operations to realize this direct image registration are translation, rotation and stretching. The direct environment that has a fixed position with respect to the markers, including the stent, may be frozen as well. The environment further away, however, may move, from frame to frame due to the motion of the heart and respiration.

Averaging of the frozen frames may lead thus to a much enhanced contrast of the environment of the markers, and therefore of the stent, whereas all structures and noise of surrounding areas may be smoothed out with a subsequent loss of contrast. In this way the stent visibility may be much enhanced.

These and other aspects of the present invention will become apparent from and elucidated with reference to the embodiment described hereinafter.

An exemplary embodiment of the present invention will be described in the following, with reference to the following drawings.

The illustration in the drawings is schematically. In different drawings, similar or identical elements are provided with similar or identical reference signs.

Figure 1:
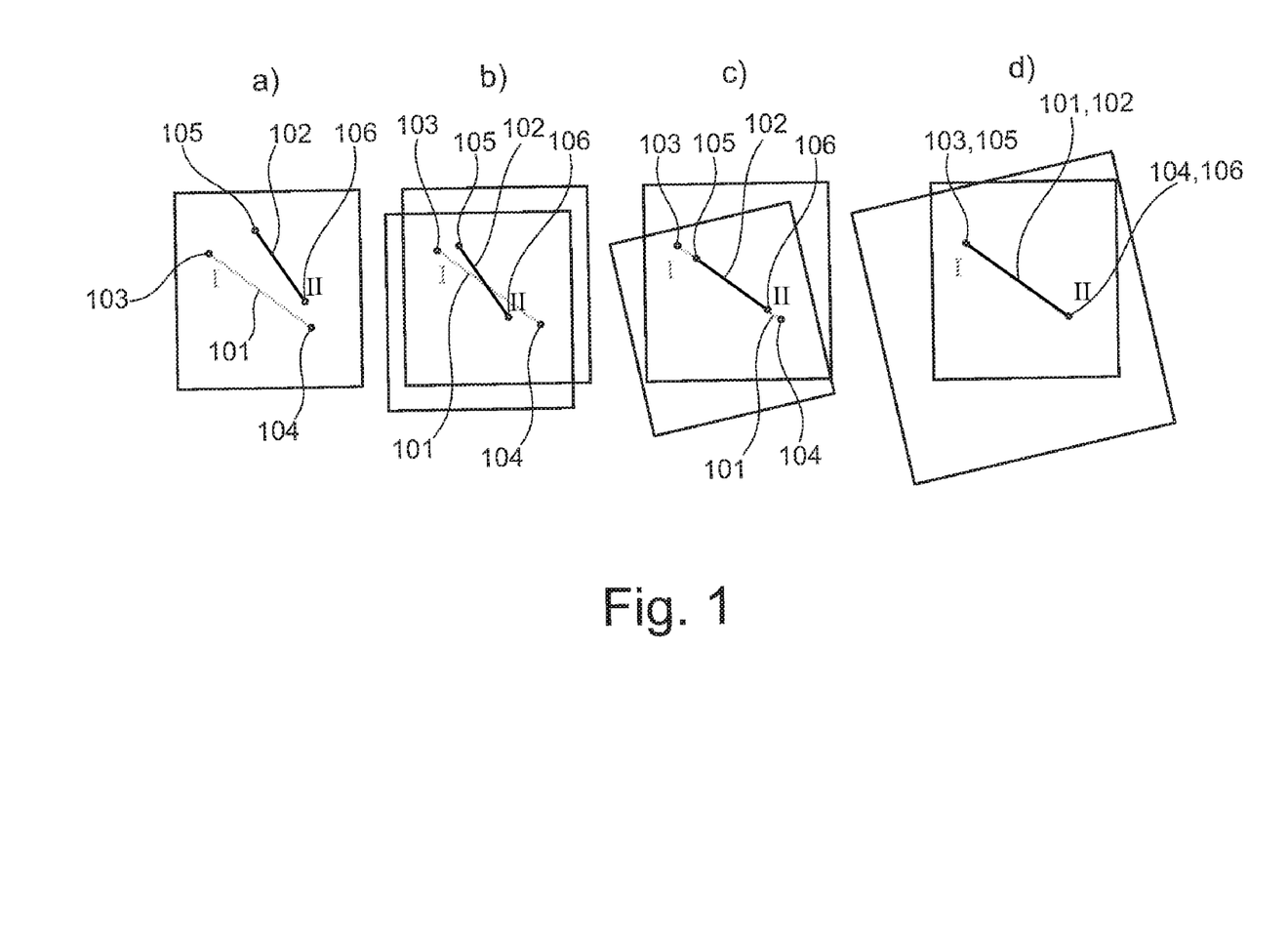
FIG. 1 shows a simplified schematic representation of registration steps.

FIG. 1 shows a schematic representation of steps which represent the basic three operations to realize image registration. In FIG. 1a two images of the same object are schematically shown by the lines 101 and 102, wherein the dots 103 and 104 of line 101 represent two markers associated with line 101 and the dots 105 and 106 of line 102 represent two markers associated with line 102. The two images of the object (line) are not matching each other. In a first step, i.e. from FIG. 1a to FIG. 1b, a translation of the image of line 102 is performed. In a second step, i.e. from FIG. 1b to FIG. 1c, a rotation of the image of line 102 is performed, while in a third step, i.e. from FIG. 1c to FIG. 1d, a stretching, or scaling of the image of line 102 is performed. After these three basic steps the lines 101 and 102 coincide in FIG. 1d. The translation, rotation and stretching are done in such a way that this coincidence of the two lines, i.e. objects, is achievable. Afterwards the two images are matched to each other, i.e. registered, and can be subtracted from or added to each other. FIG. 1 may be seen as a schematic example of registration steps to align balloon markers in selected frames I and II of a stent sequence, wherein processing steps are a) automatic marker extraction in frame I and II, b)translation, c) rotation, and d) stretching.

Figure 2:
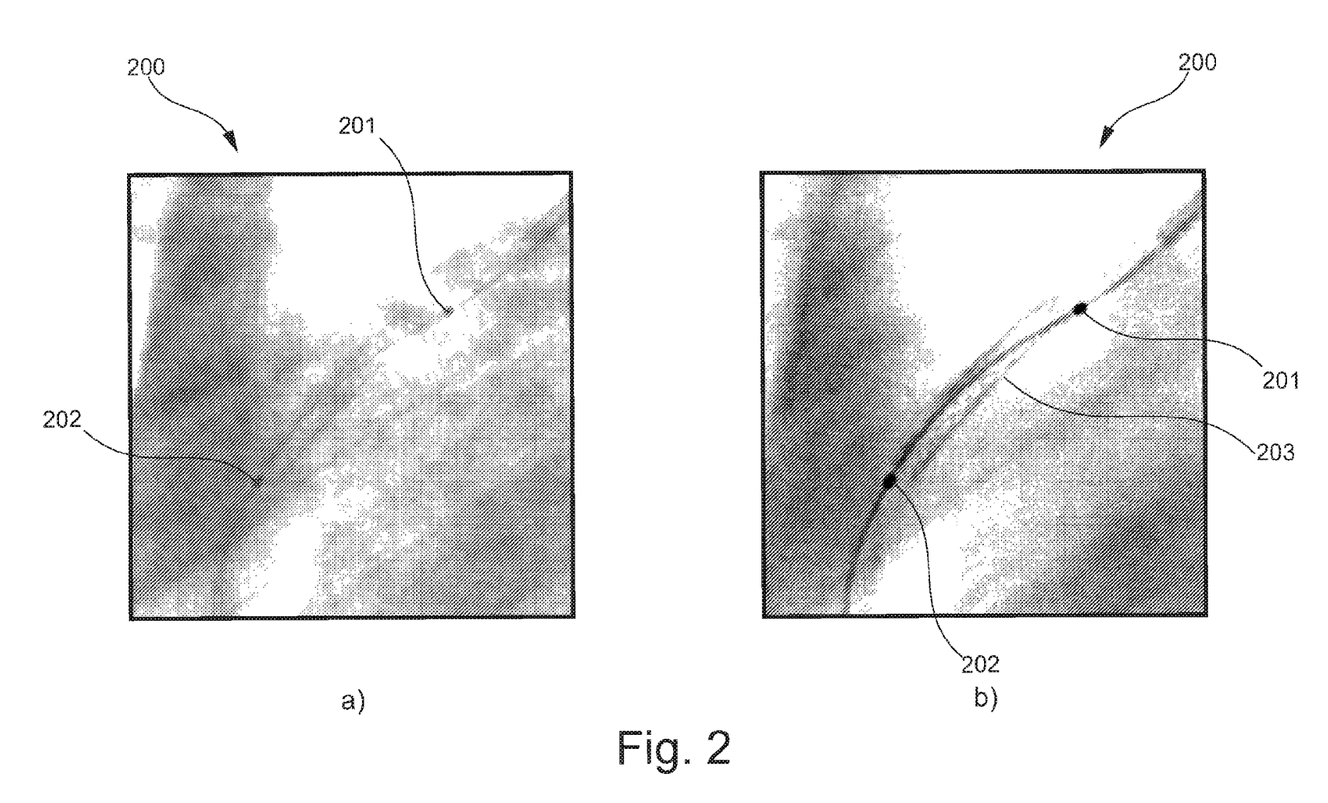
FIG. 2 shows a schematic view of a typical stent enhancement.

FIG. 2 shows a schematic view of a typical stent enhancement. In particular, FIG. 2a shows an image before an enhancement, so that in FIG. 2a two markers 201 and 202 having a low contrast to the surrounding areas can be slightly seen. FIG. 2a represents an original stent image. When performing an enhancement the software freezes the position and orientation of the markers 201 and 202 (with respect to each other) in every frame (image) of the run and match the position of the markers to the positions in the first frame. The direct environment that has a fixed position with respect to the markers, including a stent 203, is frozen as well. The environment further away, however, moves, from frame to frame due to the motion of the heart and respiration.

Averaging or adding of the frozen frames leads thus to a much enhanced contrast of the environment of the markers, and therefore of the stent, whereas all structures and noise of surrounding areas are smoothed out with a subsequent loss of contrast. In this way the stent visibility is much enhanced. FIG. 2b schematically shows an image after enhancement. In FIG. 2b not only the markers 201 and 202 are clearly visible but also the stent 203 can be seen with quite good contrast with respect to the surrounding areas, i.e. a blurred background. FIG. 2b shows an enhanced static stent after balloon marker registration and temporal averaging.

The method described above leads to a static view of the enhanced stent, but without information of the coronary vessel itself. Because the vessels are not visible, or at least only visible in a rather bad quality in the enhanced image, it is not possible to use this tool to evaluate correct longitudinal placement of the stent or to see correct apposition of the stent to the vessel wall. Even if the stent has no dents it may not be in contact with the vessel wall along its entire length.

Figure 3:
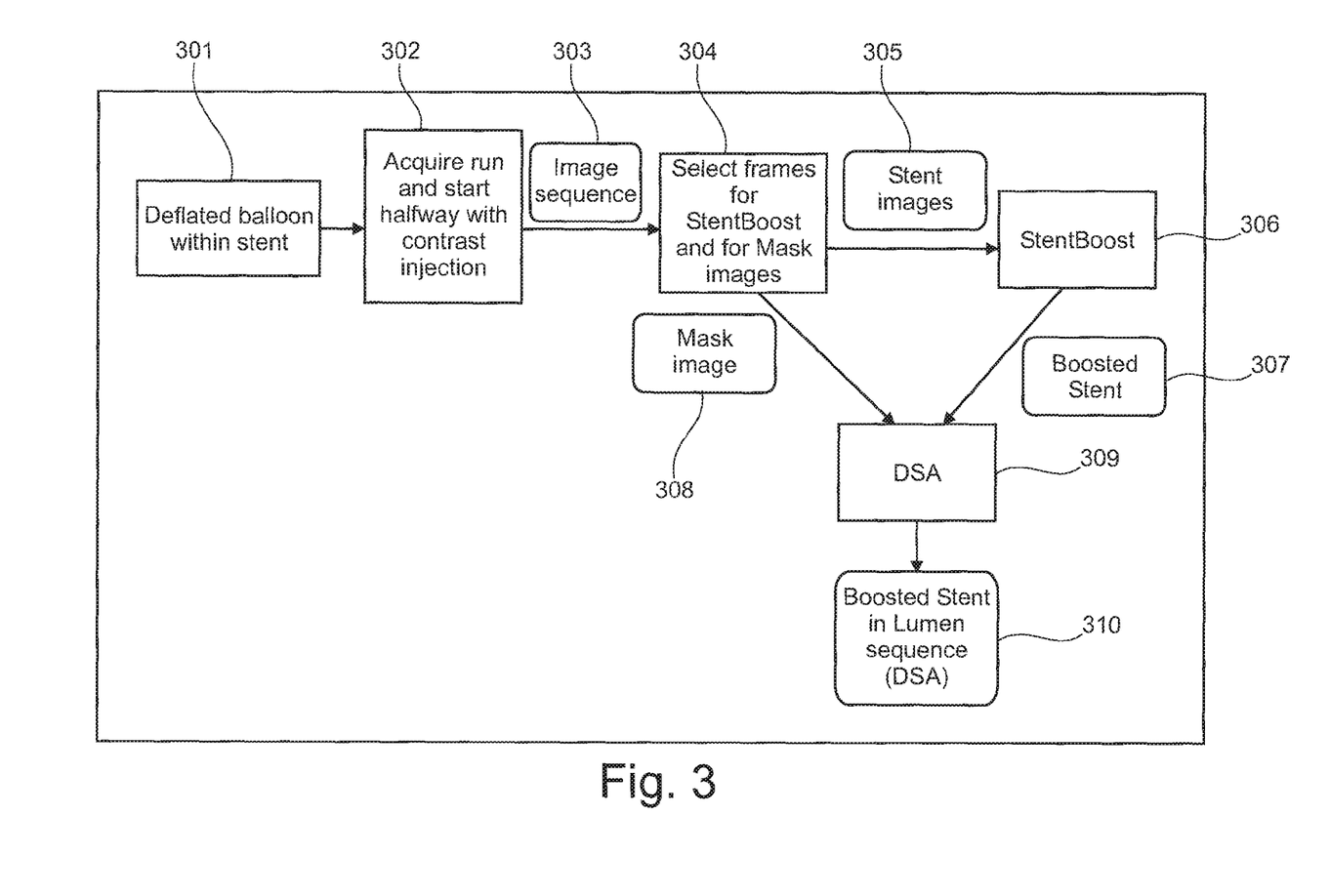
FIG. 3 shows a schematic flowchart of a method for recording data and producing an image.

FIG. 3 shows a schematic layout of measures of a physician or technician in acquiring measured data and the method for producing an image from these data.

When the stent is positioned at the desired location inside a vessel the balloon will be deflated within the stent 301. Afterwards, or before, the introducing of the stent the physician can select a desired setting at a measuring device, e.g. a X-ray system. After the balloon is deflated a first set of raw data is taken, i.e. the physician or a technician starts to take a cine series. After some time, i.e. after taking data for some images, a contrast agent is injected into the vessel 302 and a second set of raw data is taken. While recording the raw data the balloon with the markers needs to be present inside the stent. The raw data are automatically transferred to a processing unit, e.g. a workstation or PC. The processing unit generates raw images from the raw data. Preferably, the raw images are marked in such a way that they are identifiable as images relating to a run from which an enhanced image according to an embodiment of the present invention shall be reconstructed, e.g. a so called "StentBoost Substract run". Such a marking can be implemented as an identifier string in the raw images. For example, a real-time link can be used to provide a fast raw data and/or raw image transfer. The resulting sequence of raw images may be transferred to another working station or can be processed further in the same working station 303. The raw images can be displayed on a monitor so that the physician can select a Region of Interest (ROI). However, the determination of the Region Of Interest can also be done automatically, e.g. in an image recognition. Such an automatically placement may be in particular suitable for the first set of raw data, i.e. the raw data which are recorded without an influence of the contrast agent. Further, the raw images (frames) are selected for an intermediate image and a mask image 304.

After the selection, which can be done automatically, e.g. by using an intensity of the raw image, e.g. the contrast and/or brightness, a mask image is determined from the images relating to the second subset of raw data, while the images of the first subset of raw data are used to generate an intermediate image which is enhanced 305. This process may be started by the physician by pushing a button or switch. Further, the physician may choose one of several viewing options for the final image(s) which has to be generated or manual correct frame selection or marker detection.

The further steps for generating the intermediate image include a registration of the images of the first subset of raw images and an averaging of these images in order to achieve a boosted image of the stent 306. The intermediate image 307 and the mask image 308 are then subtracted from each other 309 in order to generate a final image. In case several final images are generated, e.g. by generating one intermediate image but using a plurality of mask images, a sequence of final images can be displayed 310. For example, each image relating to the second subset of raw data, i.e. which are recorded under the influence of the contrast agent, can be used as a single mask image, so that a sequence of final images can be produced visualising an inflow of the contrast agent into the stent. Such a final image or sequence of final images may be advantageous to evaluate stent placement in relation to collateral vessels and to evaluate stent apposition, since the final image(s) shows the contrast filled vessels and the enhanced view of the stent.

Figure 4:
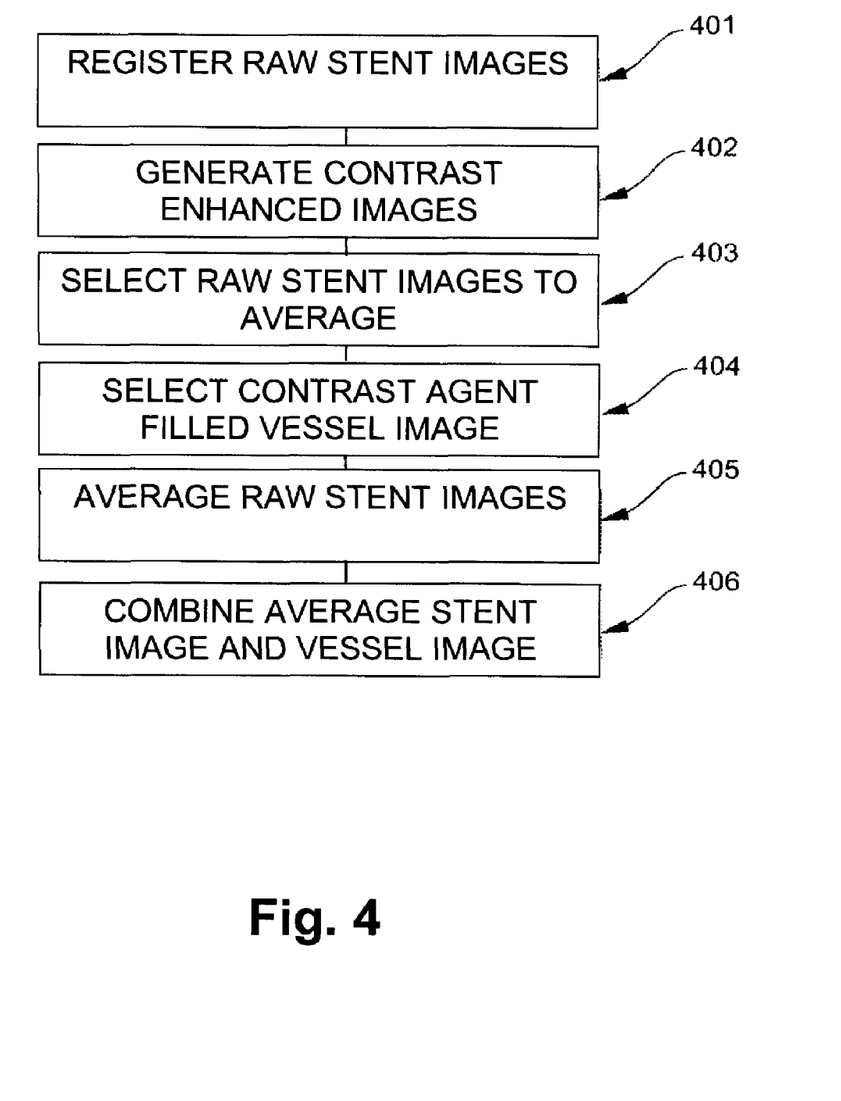
FIG. 4 shows a schematic flowchart of a method for producing an image according to an embodiment of the present invention.

In the following the arithmetic workflow of the method according to an exemplary embodiment of the invention will be again shortly described with reference to FIG. 4. In FIG. 4 the method starts with the detecting of the markers in all raw images in order to register the raw images 401. Frames (raw images) with unreliable markers, i.e. not clearly visible markers, are automatically rejected. Afterwards the contrast agent is detected in a limited area around the markers in order to distinguish between the first subset of raw images relating to the first subset of raw data and the second subset of raw images, which are taken under the influence of the contrast agent 402. This can be done according to an image intensity or optionally by so-called vessel tracking or other known methods.

After the contrast agent is detected in every raw image, a start of inflow of the contrast agent into the stent can be determined, i.e. an image is determined which is the last belonging to the first subset of images, which can be used for the enhancement of the stent image (StentBoost image) 403. Out of the frames which does not belong to this first subset of raw images one single frame is detected with a good filling of contrast agent in the vessels, i.e. the vessel in which the stent is introduced and the collaterals need to be properly filled with the contrast agent 404. Probably a frame at a later stage of contrast filling is most appropriate.

Afterwards the so-called Boostimage, i.e. the intermediate image, of the stent is created using the raw images preceding the contrast agent injection, i.e. which belong to the first subset of raw images 405. Then a final image, or partial subtraction image, is created, using the above described direct registration of the mask image and the intermediate image, wherein the markers are used for the direct registration. That is, the markers in the mask image are registered to the markers in the intermediate image, or the other way round. This registration, and some possible other pre-processing and post-processing corrections, are performed before the two images are subtracted from each other 406. In case the mask image is subtracted from the intermediate image the vessels will be shown in negative (light colour) while the stent will be shown in positive (dark colour). For this step Look-Up-Tables can be used, which may be especially tuned for this purpose.

For the following display of the final image or sequence of final images several viewing options can be selected.

In a first viewing mode a switching between the final image and the intermediate image can be chosen, which may improve assessment of the stent placement in relation to the vessel. Switching can be automatically blinking on and of, so-called "blinking mode", or manually by a user by a "toggle" button, so-called "toggle mode". For these modes the system or interface comprises a "blink" button and a "toggle" button. Also a playback mode can be chosen, which can be controlled by a "playback" button. In particular, the playback of the intermediate images may be controlled by such a "playback" button. During such a playback of the intermediate images the mask image can be toggled on and off.

In a second viewing mode a loop (sequence) of final images is shown, which are generated by subtracting each frame (image) belonging to the second subset of raw images, i.e. the raw images taken under the influence of the contrast agent, from the intermediate image. Thus, a "movie" is displayed showing the stent in black (or dark colour) with the contrast flowing in white (light colour). For choosing this mode the system comprises so-called "contrast inflow" button. A playback of this loop can be controlled by the "playback" button as well.

In a third viewing mode the vessels and/or stent can be segmented out of the mask and/or intermediate image and can be used as a noise free or at least noise reduced overlay. In this connection segmentation means that areas of the images, e.g. the stent and/or the vessels are cut out of the image in order to get images parts on which substantially only these areas, and the elements depicted in these parts, are present. By using this segmented images the noise in the final images may be reducible.

In a fourth viewing mode it may be possible to fade from the intermediate image to the mask image, i.e. no abrupt change (blinking or toggling) between these two images but a smoothed change is performed.

Other viewing modes may include so-called moving blinds, an registration of vessel and stent images in which both, enhanced stent and registered vessel images, are divided into a number of strips (e.g. numbered from, 1, 2, 3 ... N). Next a fusion of these images is created by taking strip 1, 3, 5, etc from the stent image, and strip 2, 4, 6, etc from the registered vessel image, and merging these strips into their correct positions. The result is an image with information mixed from both images. This may give the impression to look through blinds. Moving blinds can be created by letting the boundary of these strips move in a periodic motion in the direction perpendicular to the blinds contour, so that the blinds seems to move over the image. The number and precise direction of these blinds might be defined by the user.

Another method, is to gradually fade the (negative or positive) stent image to the (negative or positive) vessel image and vice versa.

In other viewing options other mixing options of the final image and/or intermediate image and/or mask image can be used, e.g. so-called Fluo-Fade/Smart mask modes.

Figure 5:
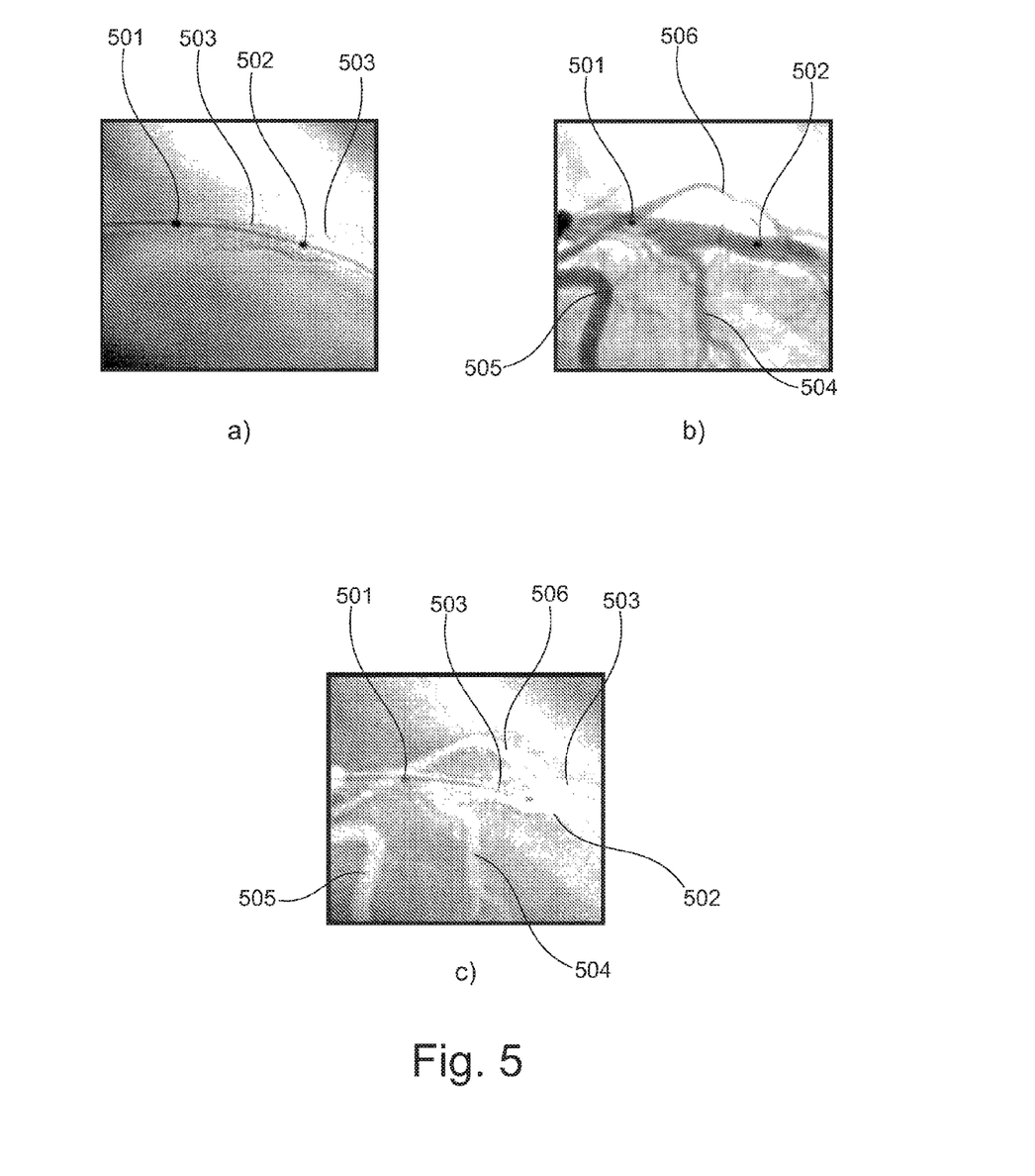
FIG. 5 shows a schematic view of an image produced according to a method according to an exemplary embodiment.

In FIG. 5 a schematic view of an image produced according to a method according to an exemplary embodiment is shown. In FIG. 5a an example of an intermediate image, i.e. an image having enhanced contrast, is shown. Two markers 501 and 502 can be clearly seen. Also a stent 503 can be seen in FIG. 5a, while the surrounding vessels are smoothed out in FIG. 5a. FIG. 5b shows an example of a mask image, in which vessels 504, 505 and 506 can be clearly seen. Furthermore, the markers 501 and 502 can be seen as well, so that a direct registration of the images depicted in FIG. 5a and in FIG. 5b can be performed. After the direct registration the two images can be subtracted from each other, e.g. the mask image can be subtracted from the intermediate image. The result of such a subtraction is shown in FIG. 5c. In FIG. 5c the markers 501 and 502 can be seen in black or dark grey as well as the stent 503, while the vessels 504, 505 and 506 are depicted in light grey. Thus, the image of FIG. 5c shows the vessels as well as the stent.

Figure 6:
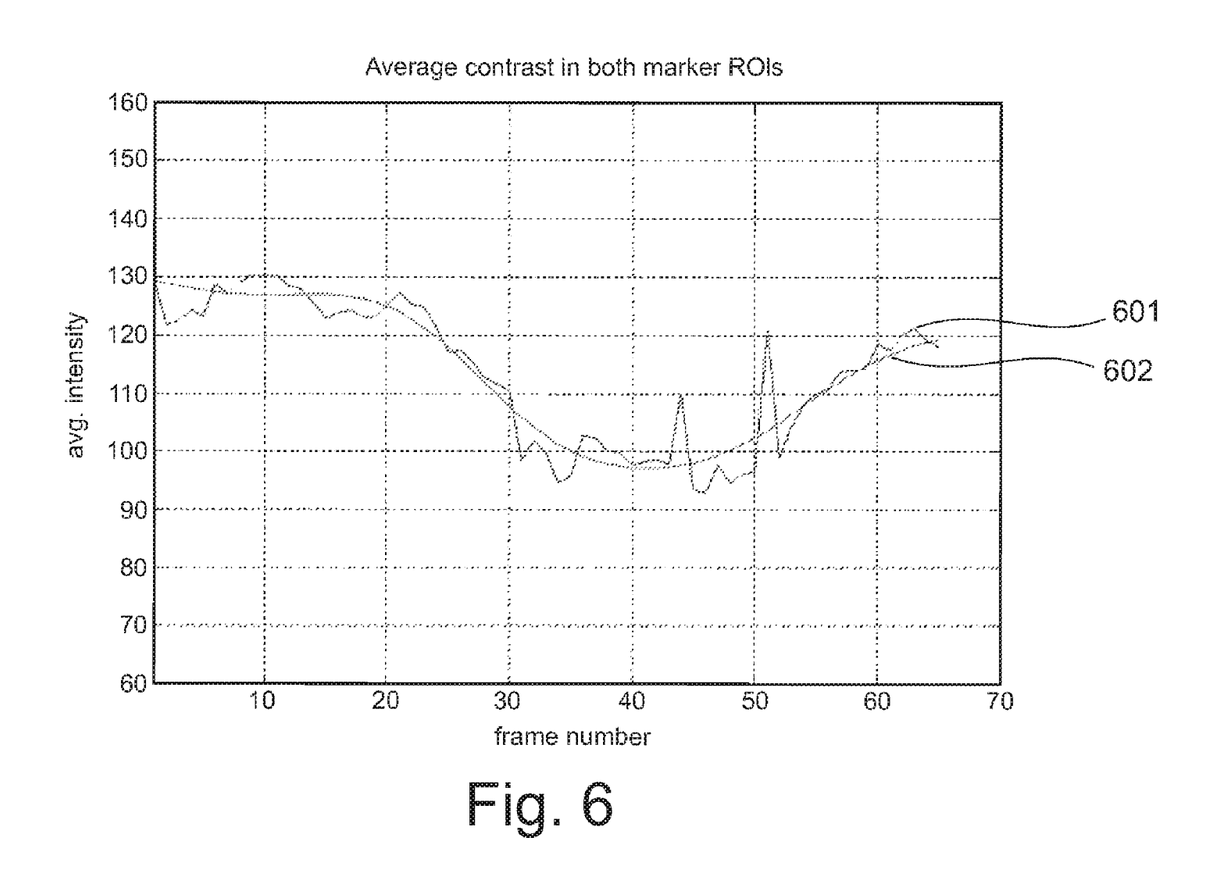
FIG. 6 shows a schematic diagram of measured contrast.

FIG. 6 shows a schematic diagram of measured contrast for the raw images of an X-ray run. The shown diagram relates to the step 402 of the algorithmic workflow, i.e. the step in which the contrast agent is detected in the region around the stent. FIG. 6 shows the average contrast, i.e. image contrast, which in X-ray images may be substantially a measure for the amount of contrast agent present in the vessel, around both markers (summed over both regions) as line 601, while line 602 relates to a low-pass filtered version of line 601. It can be seen in FIG. 6 that in the first frames (raw images) the average contrast of the image is quite high. In these first frames no contrast agent is existent in the areas around the markers. After some time, i.e. several frames later, the contrast agent reaches the regions of the markers leading to a decline in the average image contrast. Thus, the curve, in particular the smoothed curve, can be used to detect absence and/or presence of contrast agent in the coronary vessel that contains the markers. From this diagram the frames can be assigned to the first subset of raw images or to the second subset of raw images. For example, the frames 1 to 20 can be assigned to the first subset, i.e. the intermediate image can be generated out of these frames, while the mask image may be selected from the frames showing lower average contrast. For example frame 42 can be used as the mask image which exhibit substantially the lowest smoothed contrast. Another possibility would be to chose the lowest contrast of the unsmoothed curve 601, e.g. frame 46. Optionally the determination whether a frame belongs to the first subset of raw images or to the second subset of raw images, may be improved by the so-called "Frangi's filter". The Frangi filter is, for example, described in Frangi et al.,"Multiscale vessel enhancement filtering", MICCAI 1998, Boston USA, vol 1496, pp130-137, 1998, which is herby incorporated herein by reference. A Frangi filter is a method to enhance vessel (or tube like) structures and results in a feature image that represents in each pixel the likeliness that it is a vessel. By creating these images for all the raw images, and calculating for all these vesselness images the total pixel sum, it is possible to get per frame a number that indicates the total "amount" of contrast agent present in the image. The Frangi filter, in a different implementation can also create so-called blobness images, which indicate of a pixel belongs to a blob in the image. This measure can be used to improve the detection of markers, especially when they are "swimming" in dark contrast agent, which is the case when contrast agent enters the region of interest.

Summarizing it may be seen as one aspect of the present invention that a method for producing or generating an image is provided in which two images reconstructed from data taken under different circumstances from the same physical object are directly registered or matched and afterwards subtracted from each other.

It should be noted that the term "comprising" does not exclude other elements or steps and the "a" or "an" does not exclude a plurality. Also elements described in association with different embodiments may be combined. It should also be noted that reference signs in the claims shall not be construed as limiting the scope of the claims.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for producing an anatomical image, the method comprising:
receiving a plurality of raw images depicting a physical object in an anatomical region;
dividing the plurality of raw images into a first subset of primary images and a second subset of secondary images according to a predetermined criterion;
registering the physical object in the primary images and combining the primary images in the first subset to generate an intermediate image in which the physical object is enhanced and the anatomical region is deemphasized;
generating a mask image from the second subset of secondary images, the mask image enhancing a portion of the anatomical region adjacent the physical object;
registering the intermediate image and the mask image by using direct registration of predetermined features present in the intermediate image and in the mask image; and
fusing the mask image and the intermediate image to generate a fused image depicting the enhanced physical object registered with the enhanced anatomy.

2. The method according to claim 1,
wherein the fusing is done by one of the group consisting of:
subtracting the intermediate image and the mask image from each other;
overlaying the intermediate image and the mask image; and
displaying the intermediate image and the mask image in a spatial and/or temporal interlaced way.

3. The method according to claim 1,
wherein the physical object is a stent and the anatomical region includes a blood vessel in which the stent is positioned.

4. The method according to claim 1,
wherein the predetermined criterion includes dividing images generated prior to introduction of a contrast agent to the primary images and images generated after introduction of the contrast agent to the secondary images.

5. The method according to claim 1,
wherein determining the mask image comprises registering and combining several secondary images.

6. The method according to claim 1,
wherein the predetermined features are markers present in the intermediate image and the mask image.

7. The method according to claim 1,
wherein the plurality of raw images is generated from a plurality of raw data sets, which are recorded in at least two raw data recording runs.

8. The method according claim 1,
wherein the raw images belonging to the second subset of secondary images are recorded under influence of a contrast agent.

9. The method according to claim 8, further comprising:
determining a plurality of the mask images from the second subset of secondary images as the contrast agent flows in the anatomical region; and
generating a plurality of final images by subtracting the intermediate image and the plurality of mask images from each other.

10. The method according to claim 1, further comprising:
segmenting the intermediate image into at least a first part of the intermediate image depicting the physical object and a second part of the intermediate image;
segmenting the mask image into at least a first part of the mask image depicting the physical object and a second part of the mask image; and
wherein the final image is generated by subtracting the first part of the intermediate image and the first part of the mask image from each other.

11. The method according to claim 1, wherein the physical object comprises a first component and a second component, the method further comprising:
- detecting the first component in the intermediate image;
- detecting the second component in the mask image; and
- displaying the relative positions of the first and second components with respect to each other in a graphical or numerical way.

12. A system for producing an anatomical image, the system comprising:
- a diagnostic imaging system which generates a plurality of raw images;
- a processing unit programmed to:
  - divide the plurality of raw images into a first subset of primary images and a second subset of secondary images according to a predetermined criterion,
  - register and combine a physical object in the first subset of primary images to generate an intermediate image from the first subset of primary images,
  - generate a mask image from the second subset of secondary images,
  - register the intermediate image and the mask image by using direct registration of predetermined features present in the intermediate image and in the mask image,
  - fuse the mask image and the intermediate image; and
- a display unit which displays the fused image.

13. The system according to claim 12, wherein the physical object includes a stent, the mask image depicts blood flow in a vessel, and the fused image depicts the stent in the vessel such that a viewer can determine whether a portion of the blood flow passes around the stent.

14. The system according to claim 12, wherein the processor is further programmed to:
- control the display unit to display the mask image and the intermediate image on the display unit in an alternating sequence.

15. The system according claim 13, further comprising:
- a user input device controlled by a user to select which image out of the group of images consisting of the intermediate image, the mask image and the final image is displayed on the display unit.

16. The system according to claim 13, the processor is further programmed to:
- generate a cine series of final images from a plurality of the mask images and the intermediate image, the cine series of final images being displayed on the display unit.

17. A non-transitory computer readable medium which stores a program, which when executed by a processor, controls the processor to perform the steps of:
- receiving a plurality of raw images;
- dividing the plurality of raw images into a first subset of primary images containing a physical object and a second subset of secondary images which show blood flow;
- from the first subset of primary images, generating an intermediate image which shows the physical object more clearly than the raw images;
- determining a mask image from the second subset of secondary images;
- registering the intermediate image and the mask image; and
- fusing the mask image and the intermediate image to generate a final image showing the physical object in the blood flow.

18. A method of imaging a stent to verify its placement, the method comprising:
- with a diagnostic imaging system, generating anatomical images of an anatomical region including the stent and a blood vessel in which the stent is placed;
- from the anatomical images, creating an intermediate image depicting the stent and a mask image depicting blood in the blood vessel;
- registering the intermediate and mask images;
- combining the registered intermediate and mask images to create a final image depicting the stent placed in the vessel with the blood; and,
- on a display unit, displaying the final image such that a viewer can see the relative locations of the vessel, the stent, and the blood.

19. The method according to claim 18, wherein the anatomical images are generated while a catheter carrying imageable markers is positioned in the stent and the blood vessel and wherein registering the intermediate and mask images includes registering the imageable markers in the intermediate and mask images.

20. The method according to claim 19, wherein creating the intermediate image includes registering the imageable markers to register the stent in a plurality of the anatomical images and combining the registered stent images to enhance the stent.

* * * * *